United States Patent [19]

Kaplan et al.

[11] 4,180,658
[45] Dec. 25, 1979

[54] 7[-2-ALKOXYAMINO(ACETAMIDO)]CEPHALOSPORIN DERIVATIVES

[75] Inventors: Murray A. Kaplan, Syracuse; Alphonse P. Granatek, Baldwinsville; Solomon J. Nachfolger, Syracuse, all of N.Y.

[73] Assignee: Bristol-Myers Company, New York, N.Y.

[21] Appl. No.: 880,836

[22] Filed: Feb. 24, 1978

[51] Int. Cl.$^2$ ............................................. C07D 501/36
[52] U.S. Cl. ................................. 544/27; 544/19; 548/251; 260/347.3
[58] Field of Search ................................ 544/27

[56] References Cited
U.S. PATENT DOCUMENTS

| | | | |
|---|---|---|---|
| 4,025,626 | 5/1977 | Berges | 544/27 |
| 4,033,950 | 7/1977 | Cook et al. | 544/27 |
| 4,079,134 | 3/1978 | Berges | 544/27 |
| 4,098,888 | 7/1978 | Ochiai et al. | 424/246 |
| 4,146,710 | 3/1979 | Naito et al. | 544/27 |

FOREIGN PATENT DOCUMENTS 840950 8/1976 Belgium.
50-50095 7/1975 Japan.

*Primary Examiner*—David Wheeler
*Attorney, Agent, or Firm*—Herbert W. Taylor, Jr.

[57] ABSTRACT

Cephalosporins in a series having the formula

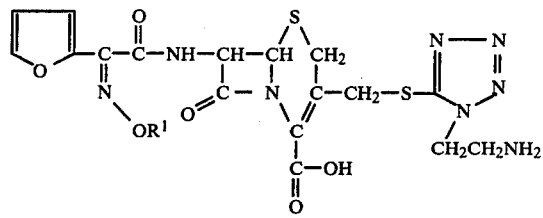

wherein $R^1$ is alkyl containing 1-4 carbon atoms or a nontoxic pharmaceutically acceptable salt thereof, were synthesized and found to be potent antibacterial agents especially when in the form of the syn isomers essentially free of the corresponding anti isomer.

8 Claims, No Drawings

7-[2-ALKOXYAMINO(ACETAMIDO)]CEPHALOSPORIN DERIVATIVES

BACKGROUND OF THE INVENTION

1. Field of the Invention

The cephalosporins of the present invention in general possess the usual attributes of such compounds and are particularly useful in the treatment of bacterial infections.

2. Description of the Prior Art

U.K. No. 1,399,086 disclosed antibiotic compounds of the general formula

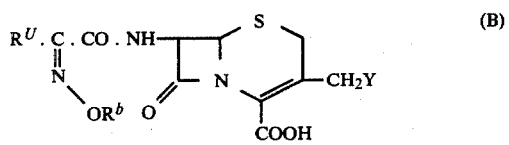

(wherein $R^U$ is phenyl; naphthyl; thienyl; furyl, benzothienyl; benzofuryl; pyridyl or any of these groups substituted by halo (chloro, bromo, iodo or fluoro), hydroxy, lower alkyl, nitro, amino, loweralkylamino, diloweralkylamino, lower alkanoyl, lower alkanoylamino, lower alkoxy, lower alkylthio or carbamoyl; $R^b$ is lower alkyl; cycloalkyl containing 3–7 carbon atoms; carbocyclic or heterocyclic aryl lower alkyl or any of these groups substituted by hydroxy, carboxy, exterified carboxy, amido, cyano, alkanoyl, amino, substituted amino, halogen or lower alkoxy; and Y is selected from acetoxy; a group of formula

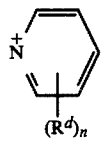

where $R^d$ and n are as defined in claim 19; a group of formula —SW where W is thiadiazolyl, diazolyl, triazolyl, tetrazolyl, thiazolyl, thiatriazolyl, oxazolyl, oxadiazolyl, benzimidazolyl, benzoxazolyl, triazolopyridyl, purinyl, pyridyl or pyrimidyl; an alkylthio group containing 1–4 carbon atoms; a group of formula —O.-CO.$R^9$ where $R^9$ is an alkyl or alkenyl group containing 2–4 carbon atoms; the group —O.CO.NH.(CH$_2$)$_m$D wherein m is an integer of from 1–4 and D is chlorine, bromine, iodine or fluorine; and azido) and non-toxic salts and esters thereof. Methods for the preparation of the starting acids used to form the 7-substituent, including their separation into syn and anti isomers, are also described therein and in U.K. No. 1,404,221.

Presently issued U.S. Pat. Nos. 3,966,717 and 3,971,778 (with many nucleophilic substituents) contain at least part of the disclosure of U.K. No. 1,399,086 as does U.S. Pat. No. 3,974,153. See also Farmdoc abstracts 17270X, 19177X and 63415X and U.S. Pat. Nos. 4,024,134, 4,007,174 and 4,066,762.

U.S. Pat. No. 3,974,153 claims compounds of the formula

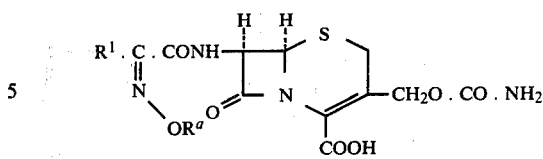

wherein $R^1$ is furyl, thienyl or phenyl; and $R^a$ is $C_{1-4}$ alkyl, $C_{3-7}$ cycloalkyl or phenyl; and a physiologically acceptable salt thereof.

With reference to cephalosporins in which the acetoxy group in the 3-methyl substituent has been displaced by a thiol see U.S. Pat. No. 3,741,965 for a review of the older art.

For examples of publications in the scientific literature see Ryan et al., Antimicrobial Agents and Chemotherapy, 9, 520–525 (1976) and O'Callaghan et al., ibid., 9, 511–519 (1976) and Norby et al., ibid., 9, 506–510 (1976) regarding cefuroxime.

West Germany No. 2,451,480 (Farmdoc 32820W) apparently teaches a method for the preparation of thiols of the formula

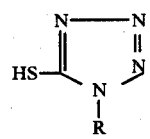

where R includes aminoethyl and there is further disclosure of that compound, methods for its preparation and its possible use to make a cephalosporin in U.K. Nos. 1,489,609, 1,489,610 and 1,461,948. See also Farmdoc 02692X, 68777X, 23652Y, 27138Y, 30744Y, 69415Y, 72915Y and U.S. Pat. No. 4,039,536.

SUMMARY OF THE INVENTION

One of the problems presently facing the medical profession at this time was described by Arnold L. Smith, M.D. in an article titled Antibiotics and Invasive *Haemophilus influenzae*, N. Engl. J. Med., 294(24), 1329–1331 (June 10, 1976) in which the opening sentence reads as follows: "Recently the information service of the Center for Disease Control, the Medical Letter and the American Academy of Pediatrics have sounded the alert that invasive strains of *Haemophilus influenzae* isolated throughout the United States have been found to be resistant to ampicillin, many of the isolates being associated with treatment failure." His concluding paragraph reads: "The current situation portends a dismal future for the antibiotic treatment of invasive *H. influenzae* disease. An *H. influenzae* resistant to the second-line drug, chloramphenicol, has been described, and, more recently, an untypable *H. influenzae* resistant to chloramphenicol and tetracycline was isolated from the throat of a four-year-old girl. Thus, both these currently efficacious agents may not be useful in the future."

A solution to this problem is provided by the present invention.

The present invention thus provides compounds having the formula

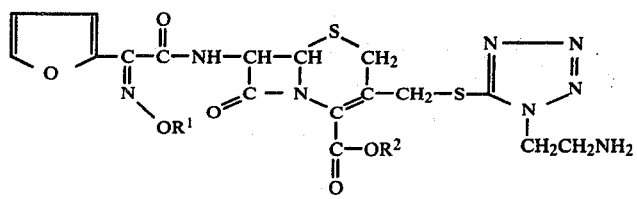

often written herein as

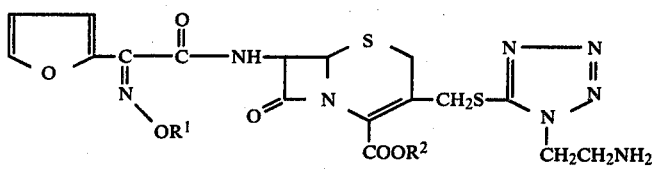

wherein R¹ is alkyl containing 1-4 carbon atoms and R² is hydrogen or a conventional, pharmaceutically acceptable, easily hydrolyzed ester forming group such as those set forth below and including the group having the formula

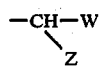

wherein when W represents hydrogen, Z represents (lower)-alkanoyl, benzoyl, naphthoyl, furoyl, thenoyl, nitrobenzoyl, methylbenzoyl, halobenzoyl, phenylbenzoyl, N-phthalimido, N-succinimido, N-saccharino, N-(lower)alkylcarbamoyl, (lower)alkoxy, (lower)alkylthio, phenoxy, carbalkoxy, carbobenzoxy, carbamoyl, benzyloxy, chlorobenzyloxy, carbophenoxy, carbo-tert.-butoxy or (lower)alkylsulfonyl, and when W represents carbalkoxy, Z represents carbalkoxy and, when W represents phenyl, Z represents benzoyl or cyano or wherein W and Z taken together represent 2-oxocycloalkyl containing 4 to 8 carbon atoms inclusive.

As set forth below in more detail the present invention also provides metallic salts of these acids and acid addition salts of these esters in addition to the "free acid" form, i.e. R is hydrogen, which exists primarily as a zwitterion. The "free acid" or zwitterion form may also be converted by treatment with a nontoxic, pharmaceutically acceptable acid to an acid addition salt of the amino group, e.g. formate or hydrochloride. The stereochemistry of the bicyclic nucleus is that found in cephalosporin C.

The compounds of the present invention are syn isomers or else are mixtures of syn and anti isomers containing at least 75% of the syn isomer. Preferably such mixtures of isomers contain at least 90% of the syn isomer and not more than 10% of the anti isomer. Most preferably the compounds are syn isomers essentially free of the corresponding anti isomer.

The preferred embodiments of the present invention are the syn isomers of the compounds of Formula I wherein R¹ is methyl or ethyl and R² is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl.

Reference to the syn (cis) isomeric form refers to the configuration of the group OR¹ with respect to the carboxamido group.

The present invention also provides the process for the production of the antibacterial agents having the formula

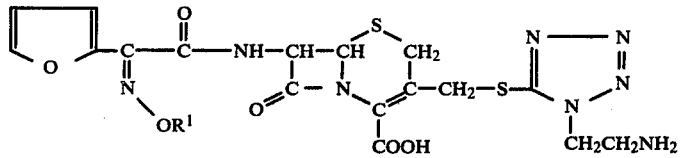

wherein R¹ is alkyl containing 1-4 carbon atoms which comprises reacting a compound of the formula

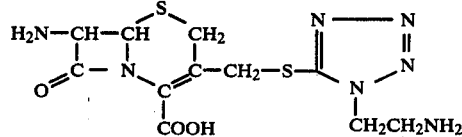

or a salt or easily hydrolyzed ester or Schiff base as with benzaldehyde or salicylaldehyde thereof (including, but not limited to, those of U.S. Pat. No. 3,284,451 and U.K. No. 1,229,453 and any of the silyl esters described in U.S. Pat. No. 3,249,622 for use with 7-aminopenicillanic acid and used in Great Britain No. 1,073,530 and particularly the pivaloyloxymethyl, acetoxymethyl, methoxymethyl, acetonyl, phenacyl, p-nitrobenzyl, β,β,β-trichloroethyl, 3-phthalidyl and 5-indanyl esters) thereof with an organic monocarboxylic acid chloride or a functional equivalent thereof as an acylating agent.

Such functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acids such as diphenylacetic acid. In addition, an acid azide or an active ester or thioester (e.g. with p-nitrophenyl, 2,4-dinitrophenol, thiophenol, thioacetic acid) may be used or the free acid itself may be coupled with compound II after first reacting said free acid with N,N'-dimethylchloroformiminium chloride [cf. Great Britain No. 1,008,170 and Novak and Weichet, *Experientia XXI*, 6, 360 (1965)] or by the use of enzymes or of an N,N'-carbonyldiimidazole or an N,N'-carbonylditriazole [cf. South African patent specification No. 63/2684] or a carbodiimide reagent [especially N,N'-dicyclohexylcarbodiimide, N,N'-diisopropylcarbodiimide or N-cyclohexyl-N'-(2-morpholinoethyl)carbodiimide; cf. Sheehan and Hess. *J. Amer. Chem. Soc.*, 77, 1967 (1955)], or of alkylylamine reagent [cf. R. Buijle and H. G. Veihe, *Angew, Chem. International Edition* 3, 582, (1964)] or of an isoxazolium salt reagent [cf. R. B. Woodward, R. A. Olofson and H. Mayer, *J. Amer. Chem. Soc.*, 83, 1010 (1961)], or of a ketenimine reagent [cf. C. L. Stevens and M. E. Munk, *J. Amer. Chem. Soc.*, 80, 4065 (1958)] or of hexachlorocyclotriphosphatriazine or hexabromocyclotriphosphatriazine (U.S. Pat. No. 3,651,050) or of diphenylphosphoryl azide [DPPA; *J. Amer. Chem. Soc.*, 94, 6203–6205 (1972)] or of diethylphosphoryl cyanide [DEPC; Tetrahedron Letters No. 18, pp. 1595–1598 (1973)] or of diphenyl phosphite [Tetrahedron Letters No. 49, pp. 5047–5050 (1972)]. Another equivalent of the acid chloride is a corresponding azolide, i.e., an amide of the corresponding acid whose amide nitrogen is a member of a quasiaromatic five membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolide. The by-product, imidazole, precipitates and may be separated and the imidazolide isolated, but this is not essential. The methods for carrying out these reactions to produce a cephalosporin and the methods used to isolate the cephalosporin so produced are well known in the art.

Mention was made above of the use of enzymes to couple the free acid with compound II. Included in the scope of such processes are the use of an ester, e.g. the methyl ester, of that free acid with enzymes provided by various microorganisms, e.g. those described by T. Takahashi et al., *J. Amer. Chem. Soc.*, 94(11), 4035–4037 (1972) and by T. Nara et al., J. Antibiotics (Japan) 24(5), 321–323 (1971) and in U.S. Pat. No. 3,682,777.

For the coupling of the organic carboxylic acid as described above with compound II (or a salt or preferably an easily hydrolyzed ester of Schiff base, as with benzaldehyde, thereof) it is also convenient and efficient to utilize as the coupling agent phosphonitrilic chloride trimer (J. Org. Chem., 33(7), 2979–81, 1968) or N-ethoxy-1,2-dihydroquinoline (EEDQ) as described in J. Amer. Chem. Soc., 90, 823–824 and 1652–1653 (1968) and U.S. Pat. No. 3,455,929. The reaction is preferably carried out at 30°-35° C. in benzene, ethanol or tetrahydrofuran using about equimolar quantities of all three reagents followed by conventional isolation and removal by conventional methods of any blocking groups present.

An additional process of the present invention comprises the preparation of the compounds of the present invention by the displacement of the 3-acetoxy group of a 7-acylaminocephalosporanic acid (prepared by substituting 7-aminocephalosporanic acid for the 3-thiolated-7-aminocephalosporanic acids in the acylation procedures described herein and elsewhere reported) with a thiol $HSR^3$ having the formula

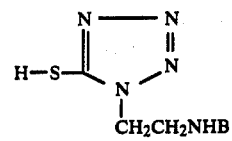

wherein B is hydrogen or a protecting group for a primary amine and then removing the protecting group if any is present, as on the aminoethyl group and/or the carboxyl group.

The displacement of such a 3-acetoxy group with such a thiol may be accomplished in solution as in water or aqueous acetone at a temperature of at least room temperature and preferably within the range of about 50° to 100° C. in the presence of a mild base such as sodium bicarbonate, e.g. preferably near neutrality such as at about pH 6. An excess of the thiol is preferably employed. The reaction product is isolated by careful acidification of the reaction mixture followed by extraction with a water-immiscible organic solvent. As noted above, the preparation of many other 7-acylamidocephalosporanic acids is described in the patent and scientific literature, e.g. in U.S. Class 260-243 C.

The salts of the compounds of this invention include the nontoxic carboxylic acid salts thereof, including nontoxic metallic salts such as sodium, potassium, calcium and aluminum, the ammonium salt and substituted ammonium salts, e.g. salts of such nontoxic amines as L-lysine, arginine, histidine, trialkylamines including triethylamine, procaine, dibenzylamine, N-benzylbeta-phenethylamine, 1-ephenamine, N,N'-dibenzylethylenediamine, dehydroabietylamine, N,N'-bis-dehydroabietylethylenediamine, and other amines which have been used to form salts with benzylpenicillin and also nontoxic acid addition salts (of the primary amino group) thereof including the mineral acid addition salts such as the hydrochloride, hydrobromide, hydroiodide, sulfate, sulfamate and phosphate and the organic acid addition salts such as the maleate, acetate, citrate, oxalate, succinate, benzoate, tartrate, fumarate, malate, mandelate, ascorbate, formate and the like.

The preferred esters of the cephalosporins of the present invention are the pivaloyloxymethyl, acetoxymethyl, methoxymethyl, acetonyl and phenacyl esters. All are useful intermediates in the production of the cephalosporin having a free carboxyl group.

As indicated above, these five esters of 7-aminocephalosporanic acid are each prepared by known methods. One excellent procedure is that of U.S. Pat. No. 3,284,451 in which sodium cephalothin is esterified by reaction with the corresponding active chloro or bromo compound (e.g. phenacyl bromide, chloroacetone, chloromethyl ether, pivaloyloxymethyl chloride [also called chloromethyl pivalate], acetoxymethyl chloride) and then the thienylacetic acid sidechain is removed enzymatically as in the same patent or chemically as in U.S. Pat. No. 3,575,970 and in Journal of Antibiotics, XXIV (11), 767–773 (1971). In another good method the triethylamine salt of 7-aminocephalosporanic acid is reacted directly with the active halogen compound, as in United Kingdom No. 1,229,453.

These esters of 7-aminocephalosporanic acid are then reacted with the nucleophile $HSR^3$ in the same manner as is illustrated herein for 7-aminocephalosporanic acid itself. The 3-thiolated ester of 7-aminocephalosporanic acid is then coupled with the organic carboxylic acid as before.

The ester of the cephalosporin so obtained is, if not used per se, converted to its free acid and, if desired, any salt by removal of the esterifying group, as by aqueous or enzymatic hydrolysis (as with human or animal serum) or acidic or alkaline hydrolysis or by treatment with sodium thiophenoxide as taught in U.S. Pat. No. 3,284,451 and, in the penicillin series, by Sheehan et al., J. Org. Chem. 29(7), 2006–2008 (1964).

In another alternative synthesis, the 3-thiolated 7-aminocephalosporanic acid is prepared as described herein and then acylated at the 7-amino group and finally esterified, as by reaction of the appropriate alcohol with the acid chloride prepared, for example, by reaction of the final cephalosporin with thionyl chloride or by other essentially acidic esterification procedures.

In the treatment of bacterial infections in man, the compounds of this invention are administered parenterally in an amount of from about 10 to 90 mg./kg./day and preferably about 14 to 50 mg./kg./day in divided dosage, e.g. two to four times a day. They are administered in dosage units containing, for example, 125, 250 or 500 mg. of active ingredient with suitable physiologically acceptable carriers or excepients. The dosage units are in the form of liquid preparations such as solutions or suspensions and preferably are aqueous solutions of a sodium, potassium, hydrochloride or formate salt which are injected intravenously or intramuscularly or by continuous or intermittent infusion in concentrations of about 125–500 mgm./ml., and preferably, 250 mgm./ml. as is customary in therapy with cephalosporin antibiotics.

STARTING MATERIALS

2-Furoylcyanide

To a suspension of 26.1 g. (0.4 mole) of ground potassium cyanide in 300 ml. of acetonitrile at 5° C. was added 26.1 g. (0.2 mole) of α-furoyl chloride while keeping the temperature below 8° C. The mixture was stirred in the cold for 15 minutes then heated at reflux for 30 minutes. The reaction was cooled, filtered and the acetonitrile was removed at 15 mm. (steam-bath) leaving 24.5 g. of a dark oil which was used without further purification. An infrared spectrum showed a nitrile band at 2265 cm$^{-1}$.

2-Furaneglyoxylic Acid

The 24.5 g. of crude 2-furoylcyanide was mixed with 160 ml. concentrated hydrochloric acid at 25° C. with intermittent stirring. The reaction was stored for 24 hours at 25° C. and diluted with 80 ml. of water. The reaction was stirred for 5 minutes and filtered. The filtrate was saturated with sodium chloride and extracted with 5×120 ml. of 1:1 ether-ethyl acetate solution. The extracts were combined, dried over anhydrous magnesium sulfate and evaporated at 30° C. (15 mm.) to give a brownish-orange solid. The solid was dissolved in methanol, treated with charcoal and evaporated under reduced pressure (15 mm.) to dryness to yield 17 g. of the acid.

The product was recrystallized from toluene to give 11.5 g. (m.p. 76° C.). The IR and NMR spectra were consistent for the structure.

2-Methoxyimino-2-furylacetic Acid

To a solution of 4.5 g. (0.032 mole) of 2-furaneglyoxylic acid in 40 ml. of 50% alcohol and 3.1 g. (0.037 mole) of methoxyamine hydrochloride in 6 ml. water at 20° C. was added dilute sodium hydroxide solution to pH 4–5. The solution was stirred at pH 4–5 at 25° C. for 24 hours. The alcohol was removed under reduced pressure (15 mm.) and the solution was adjusted to pH 7–8 with 50% sodium hydroxide solution. The reaction was washed with 3×50 ml. of ether and the aqueous layer was adjusted to pH 1.9 using concentrated hydrochloric acid. The mixture was extracted with 5×50 ml. of ethyl acetate. The ethyl acetate extracts were combined, washed with brine, dried over anhydrous magnesium sulfate and evaporated under reduced pressure (15 mm.) to an oil which was cooled for one hour in an ice bath. The product was slurried with Skellysolve-B and collected to yield 3.1 g. of yellow crystals, m.p. 78° C. An analytical sample was recrystallized from toluene, dried for 16 hours in vacuo over $P_2O_5$ at 25° C. The IR and NMR spectra were consistent for the structure.

Anal. Calc'd for $C_7H_7NO_4$: C, 49.65; H, 4.17; N, 8.28. Found: C, 49.30; H, 4.21; N, 8.37.

"Skellysolve-B" is a petroleum ether fraction of b.p. 60°–68° C. consisting essentially of n-hexane.

2-Ethoxyiminofurylacetic Acid 7.85 g. (0.056 mole) of furyl-2-glyoxylic acid (2-furaneglyoxylic acid) was dissolved in 100 ml. of water and adjusted to pH 7 with 50% sodium hydroxide. 6.83 g. of ethoxyamine hydrochloride in 10 ml. of water was added, while keeping the pH at 4–5. The reaction was diluted with 25 ml. of alcohol, stirred 3 hours at room temperature and then filtered. The alcohol was removed at 35° C. (15 mm.) and the aqueous portion was adjusted with dilute sodium hydroxide solution to pH 7–8 and then was washed with ether and the washes were discarded. The aqueous fraction was adjusted with 6 N hydrochloric acid to pH 1.5 and extracted into 3×80 ml. of ethyl acetate. The acetate fractions were combined, washed with brine and reduced in volume at 35° C. (15 mm.) to an oil. The oil was cooled in an ice bath, triturated with "Skellysolve-B", collected and dried over $P_2O_5$ in vacuo at 25° C. Yield: 4.8 g., m.p. 83°–85° C. The IR and NMR were consistent for the structure.

Anal. Calc'd for $C_8H_9NO_4$: C, 52.46; H, 4.95; N, 7.65. Found: C, 52.22; H, 4.94; N, 7.60.

Sodium α-Ethoxyimino-α-(2-furyl)acetate

To 50 ml. of methanol was added 250 mg. (0.0109 mole) of metallic sodium and stirred until all the sodium had dissolved. This sodium methoxide solution was treated with 2.0 g. (0.0109 mole) of α-ethoxyimino-α-(2-furyl)acetic acid dissolved in 10 ml. of methanol and stirred at room temperature for one hour. The methanol was removed at 40° C. (15 mm.) and the product was dried in vacuo over $P_2O_5$ at 25° C. to yield 2.22 g. white solid, m.p. decomp. >240° C. The IR and NMR were consistent for the structure.

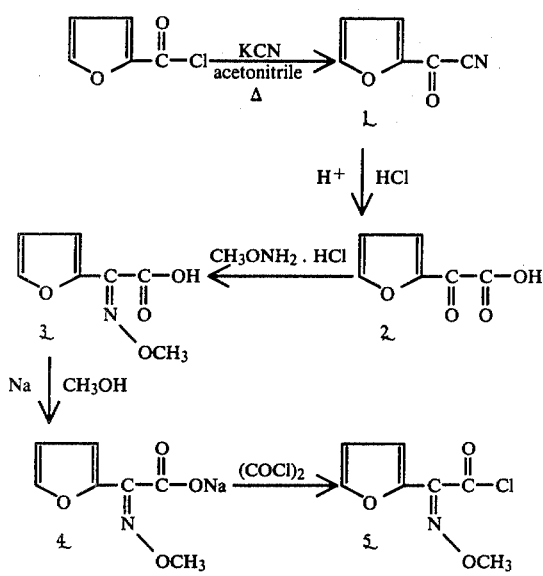

2-Furoylcyanide 1

To a suspension of 78.3 g. of powdered potassium cyanide in 900 ml. acetonitrile at 5° C. was added 59.25 ml. (68.5 g.) of α-furoyl chloride with vigorous stirring while keeping the temperature at 4°–8° C. The mixture was stirred at 4°–8° C. for 15 minutes and then heated at reflux for 30 minutes. The mixture was cooled to 23°–25° C., filtered and washed with 50 ml. of acetonitrile which was added to the filtrate. The acetonitrile was removed at 60° C. (15 mm.) leaving 51 g. of 1 as a dark oil. An IR spectrum showed a nitrile band at 2265 cm$^{-1}$ and an NMR spectrum showed a ratio of approximately 70/30 of product 1 furoic acid. The crude product 1 was used without further purification (49% yield of product).

Furyl-2-glyoxylic Acid 2

The 51 g. of crude 2-furoyl cyanide 1 was mixed with 500 ml. concentrated hydrochloric acid at 25° C. The reaction was stirred for 24 hours at 25° C. and then diluted with 240 ml. of water. The mixture was stirred for 5 minutes and filtered. The black filtrate was saturated with sodium chloride and extracted with 6×500 ml. of 1:1 ether-ethyl acetate solution. (Note: Initially the extractions were difficult due to the inability to see the separation of two black phases. As additional ether-ethyl acetate extractions were run the task was simplified.) The solvent extracts were combined and evaporated to dryness at 60° C. (15 mm.). The resultant solid was dissolved in 600 ml. ether, (Note: Use of alcohols should be avoided at this point as esters may form), treated with 10 g. of charcoal ("Darko-KB"), filtered after stirring for 0.5 hour and evaporated to dryness at 50° C. (15 mm.) to yield 46.6 g. of 2 as a light, tan-colored acid. This product 2 was found to contain a ratio of approximately 56/44 of product 2/furoic acid. This represented a 63% yield of product 2.

Purification was accomplished by dissolving the above crude product 2 in H$_2$O (50 mg./ml.), titrating to pH 2.8 with HCl and extracting with 2×200 ml. of ethyl acetate. Evaporation of the ethyl acetate extracts gave 85% furoic acid and 15% product 2. The pH 2.8 aqueous phase was adjusted to pH 0.8 (HCl) and extracted with 2×200 ml. ethyl acetate. The organic extracts were combined and washed with 50 ml. H$_2$O. The organic phase was evaporated at 50° C. (15 mm.) yielding a solid with a ratio of approximately 86/14 of product 2/furoic acid. This solid was then recrystallized by dissolving the product 2 in toluene at 50 mg./ml. at 80° C., decanting, and leaving to crystallize at room temperature for 18 hours, yielding 13.3 g. of pure acid 2 by NMR. This represented a 51% yield in the purification and recrystallization step and an overall yield from the 2-furoyl chloride to the pure furyl-2-glyoxylic acid 2 of 16%.

Syn-α-methoxyiminofurylacetic Acid 3

A solution of 4.5 g. of furyl-2-glyoxylic acid 2 in 40 ml. of 50% ethanol was titrated to pH 6 with 1 N sodium hydroxide and then 3.1 g. of methoxyamine.HCl in 6 ml. of H$_2$O at 20° C. was added. The solution was titrated to a constant pH 4.9 and stirred at pH 4.9 for 24 hours at 20°–23° C. The ethanol was then removed at 50° C. (15 mm.) and the residual aqueous solution was titrated to pH 8 with 50% sodium hydroxide and washed with 3×50 ml. ether (pH adjusted to 8 after each wash). The aqueous layer was titrated to pH 1.9 with concentrated HCl and extracted with 5×50 ml. ethyl acetate with the pH readjusted to 1.9 after each extraction. The ethyl acetate extracts were combined and evaporated to a solid 3 at 50° C. (15 mm.). This solid was then slurried with 75 ml. of "Skellysolve B". The suspension was filtered and the solids were redissolved in 16 ml. of toluene at 80° C. The hot solution was decanted and left to crystallize at 20°–23° C. for 18 hours to yield 1.17 g. 3 (22% yield of product). The NMR was clean and consistent for the structure 3 with a trace of anti isomer present.

Sodium Syn-α-methoxyiminofurylacetate 4

To 40 ml. of methanol was added 0.16 g. of sodium. The mixture was stirred until all of the sodium dissolved and then decanted. The resulting sodium methoxide solution was cooled to 3° C. and 1.12 g. of syn-α-methoxyiminofurylacetic acid 3 in 7.8 ml. of methanol was added. The solution was stirred for 10 minutes at room temperature. The solvent was evaporated at 40° C. (15 mm.). The residue 4 was dried by azeotropic distillation with 3×20 ml. of benzene at 40° C. (15 mm.). The product 4 was dried for 18 hours at 23° C. under high vacuum (0.7 mm.) over P$_2$O$_5$ yielding 1.25 g. (99% yield of product). The NMR showed this product 4 to be clean and consistent for the structure with 0.15 mole methanol and a trace of anti isomer.

To 0.63 g. of sodium syn-α-methoxyiminofurylacetate 4 suspended in 25 ml. of benzene was added four drops of dry dimethylformamide and 0.31 ml. (1.1 eq.) of oxalyl chloride. This mixture was stirred for 40 minutes at 20°–23° C. The benzene was removed at 35° C. (15 mm.) to provide the acid chloride 5 as a gummy residue.

A. 2-Aminoethylacetamide

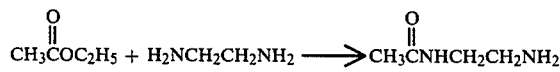

To 1915 ml. (1721.6 g.; 28.64 M.) ethylene diamine was added 933 ml. (841 g.; 9.5 M.) ethyl acetate. The reaction mixture was allowed to stand at room temperature for 5 days. The unreacted ethylene diamine was removed at 70° C. (~15 mm). The main fraction was distilled at 110°–119° and 0.8 mm to yield 642 g. (66%) (m.p.≅43° C.) of 2-aminoethylacetamide.

B. 2-Isothiocyanoethylacetamide

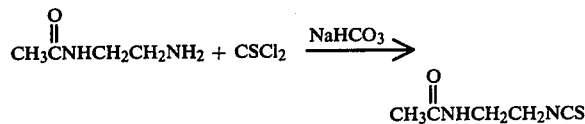

To a stirred three-phase system of 84 g. NaHCO$_3$ in 225 ml. water and 15.32 g. (0.15 M.) 2-aminoethylacetamide in 247 ml. CHCl$_3$ was added dropwise 14.3 ml. (21.56 g.; 0.187 M.) thiophosgene in 160 ml. CHCl$_3$ at room temperature. The orange mixture was stirred for 18 hours at room temperature (19°–20° C.).

The resulting yellow mixture was filtered to remove the excess NaHCO$_3$ and the two layers were separated. The water phase was washed twice with 50 ml. CHCl$_3$. The combined organic phases were washed with saturated sodium chloride solution, dried over anhydrous MgSO$_4$ and evaporated at 38°–45° C. (15 mm) to give 2-isothiocyanoethylacetamide as an oil; 27.5 g. (contaminated with CHCl$_3$). Weight corrected for 0.6 M CHCl$_3$ from NMR was 18 g. (83% yield CHCl$_3$ free).

C. 1-Acetamidoethyl-5-mercaptotetrazole

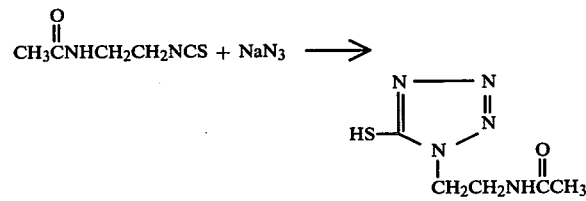

To a stirred solution of 11.3 g. (0.1738 M.) NaN$_3$ (CAUTION!) in 200 ml. water at 65° C. under N$_2$ was added dropwise 17 g. (about 0.1248 M.) 2-isothiocyanoethylacetamide in 20 ml. CHCl$_3$. The resulting mixture was stirred for 2½ hours at 75° C. and stored for 20 hours at room temperature.

The filtered solution was cooled and acidified to pH 1.5 with 6 N HCl. The sample was extracted three times with 100 ml. ethyl acetate. The EtOAc was washed with 50 ml. of saturated sodium chloride solution, dried over anhydrous MgSO$_4$ and evaporated at 40° C. (15 mm.) to a yellow solid. The solid 1-acetamidoethyl-5-mercaptotetrazole was triturated with ether, filtered, dried in vacuo and found to weigh 4.78 g. (21% yield).

D. 2-Isothiocyanoethylacetamide

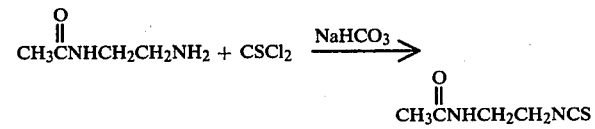

NOTE: The procedure below was run simultaneously in three separate 2-liter flasks.

To a stirred three-phase system of 168 g. NaHCO$_3$ in 450 ml. water and 30.64 g. (0.3 M.) 2-aminoethylacetamide in 494 ml. CHCl$_3$, was added dropwise 28.6 ml. (43.1 g.; 0.373 M.) thiophosgene in 320 ml. CHCl$_3$ at room temperature. The orange mixture was stirred for 18 hours at room temperature.

The resulting yellow mixture was filtered to remove the excess NaHCO$_3$ and the two layers were separated. The water phase was washed twice with 100 ml. CHCl$_3$. The combined organic phases were washed with 75 ml. saturated sodium chloride solution, dried over anhydrous MgSO$_4$ and evaporated at 40° C. (15 mm.) to oily crystals of 2-isothiocyanoethylacetamide.

| Yield: | I - 59.7 g. (26% CHCl$_3$→44.2 g.) |
| --- | --- |
| | II - 49.3 g. (15% CHCl$_3$→41.7 g.) |
| | III - 51.6 g. (15% CHCl$_3$→43.9 g.) |
| | TOTAL = 129.8 g. (100%) |

E. 1-Acetamidoethyl-5-mercaptotetrazole

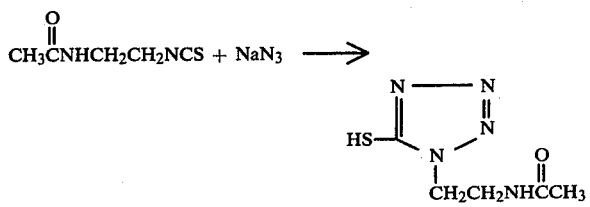

To a stirred solution of 87.6 g. (1.3477 M.) NaN$_3$ (CAUTION!) in one liter water at 65° C. under N$_2$ was added dropwise 126.7 g. (0.8786 M.) 2-isothiocyanoethylacetamide in 150 ml. CHCl$_3$. The resulting mixture was stirred for three hours 10 minutes at 70°–72° C. and then cooled to 15° C., filtered and acidified to pH 1.5 with concentrated HCl (CAUTION! hydrozoic acid is liberated). The sample was extracted four times with 500 ml. ethyl acetate. The EtOAc was washed with 300 ml. saturated sodium chloride solution, dried over anhydrous MgSO$_4$ and evaporated at 40° C. (15 mm.) to a yellow solid.

The solid was triturated with a minimum amount of ether, filtered and dried in vacuo over P$_2$O$_5$ for 5 days to give 61.3 g. of 1-acetamidoethyl-5-mercaptotetrazole (37% yield).

F. 1-Aminoethyl-5-mercaptotetrazole Hydrochloride

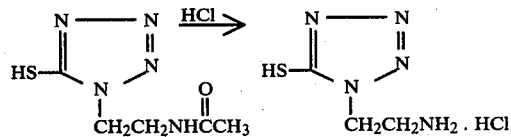

A mixture of 61.3 g. (0.3274 M.) 1-acetamidoethyl-5-mercaptotetrazole and 313 ml. 6 N HCl (196 mg./ml.; 1.888 M.) was heated at reflux for 2 hours. The resulting solution was treated with 10 g. carbon and evaporated at 45° C. (15 mm.) to a solid which was triturated with 90 ml. glacial acetic acid, washed with 250 ml. ether and dried in vacuo over P$_2$O$_5$ to give 45.6 g. (77% yield) of 1-aminoethyl-5-mercaptotetrazole hydrochloride.

G. 2-Carboethoxyethyl Isothiocyanate $$\begin{array}{l} CH_2CO_2C_2H_5 \\ | \\ CH_2NH_2 \cdot HCl \end{array} + 2(C_2H_5)_3N + CS_2 + C_2H_5OCCl \xrightarrow{(C_2H_5)_3N}$$

-continued

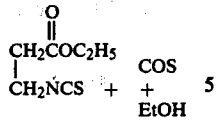

β-Alanine (178.18 g., 2 M.) was slurried in absolute ethanol (500 ml.) then gassed vigorously with HCl for 4½ hours keeping the temperature between 20°–30° C. with an ice bath. The resulting solution was then evaporated to an oil on a rotovac (50° C., 5 mm.) and azeotroped to a dry oil with 100 ml. ethyl acetate (50° C., 5 mm.). The dry oil was then crystallized by slurrying in 200 ml. ether. The crystals were collected by filtration, washed with 30 ml. of ether and dried in a desiccator over $P_2O_5$ using house vacuum for 18 hours to yield 280.4 g. (91%) β-alanine ethyl ester hydrochloride; m.p. <50° C. The NMR was consistent for the structure with about 10% unreacted β-alanine.

β-Alanine ethyl ester hydrochloride (171.3 g.; 1.11 M.) and triethylamine (TEA) (312 ml.) and 700 ml. methylene chloride were mixed together then cooled to −10° C. in an ice-acetone-salt bath. The $CS_2$ (67 ml.; 1.11 M.) in 250 ml. $CHCl_3$ was added over a 1½ hour period at a temperature of −12° to −5° C. The temperature was then allowed to warm to 10° C. and stirred at this temperature for 10 minutes. The mixture was then cooled to 0° to 5° C. and 105.7 ml. (1.11 M) ethyl chloroformate in 100 ml. $CHCl_3$ added dropwise during a 40-minute period. The mixture was stirred 30 minutes at room temperature then cooled to 0° C. TEA (156 ml.; 1.11 M) was added dropwise at 0° C. over ½ hour then stirred 3 hours at room temperature.

The mixture was stirred with 450 ml. water, separated and the organic phase was washed twice with 450 ml. 2 N HCl, twice with 450 ml. 5% $NaHCO_3$, twice with 360 ml. water, dried over $Na_2SO_4$ and then evaporated to give 148.5 g. (84% yield) of 2-carboethoxyethyl isothiocyanate as an oil.

H. 1-Carboxyethyl-5-mercaptotetrazole

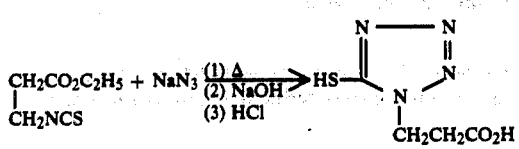

NOTE: Caution is to be taken with $NaN_3$; dust may be toxic (fatal)

110.5 g. (1.7 M.) $NaN_3$ was weighed out cautiously in the hood and dissolved in one liter water in a 2-liter R.B. 3-necked flask under $N_2$ and heated to 60° C. Using a dropping funnel, 175.0 g. (1.1 M.) 2-carboethoxyethyl isothiocyanate in 180 ml. "Skellysolve B" (mixed lower alkanes) was added and the mixture was heated to 70° C. and stirred at 70°–72° C. for 2½ hours.

The mixture was cooled to 30° C., titrated with concentrated NaOH to pH 11.5, heated to 70° C. for 40 minutes (pH 10–11.5) then cooled to 15° C., acidified to pH 2 with concentrated hydrochloric acid and extracted four times with 500 ml. ethyl acetate. The ethyl acetate extracts were washed with 400 ml of water dried over $Na_2SO_4$ and the resulting clear, yellow solution was evaporated to dryness, slurried with methylene chloride ($MeCl_2$), collected by filtration and washed with $MeCl_2$ to give 82 g. (43% yield) of 1-carboxyethyl-5-mercaptotetrazole.

I. 1-Carboxyethyl-5-diphenylmethylthiotetrazole

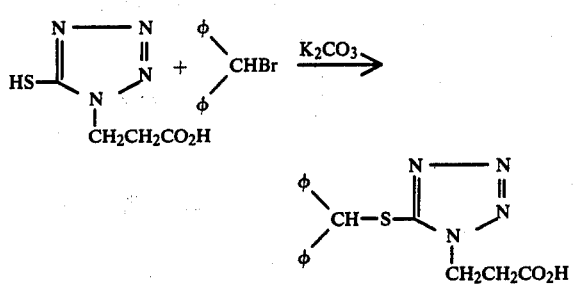

To a solution of 82 g. (0.47 M.) 1-carboxyethyl-5-mercaptotetrazole in 690 ml. dimethylformamide (DMF) was added 65 g. (0.47 M.) $K_2CO_3$ (anhydrous) and 116 g. (0.47 M.) benzhydryl bromide and the mixture was stirred 19 hours at room temperature.

The mixture was then diluted with two liters water, acidified with concentrated hydrochloric acid to pH 2 and extracted into ethyl acetate (3×1 L). The EtOAc was washed with 150 ml. water, dried with $MgSO_4$, filtered, evaporated to an oil, crystallized with one liter water, collected by filtration, washed with 500 ml. water and vacuum-dried at 50° C. to give 144.5 g. (90% yield) of 1-carboxyethyl-5-diphenylmethylthiotetrazole.

J. 1-Benzyloxycarbonylaminoethyl-5-diphenylmethylthiotetrazole

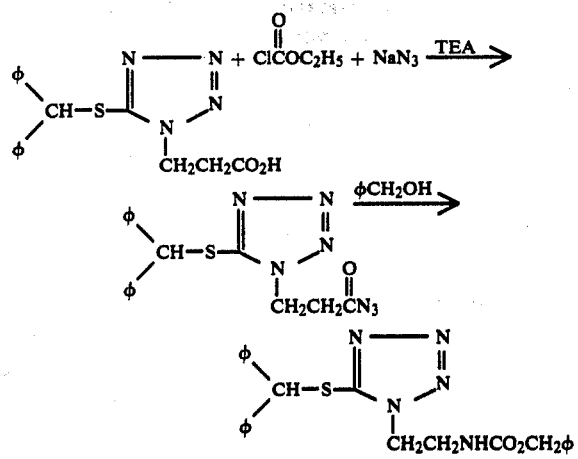

To a solution of 50.0 g. (0.1469 M.) 1-carboxyethyl-5-diphenylmethylthiotetrazole in 500 ml. tetrahydrofuran (THF) at 0°–5° C. was added 20.5 ml. TEA and 15.4 ml. (1.1 eq.) ethylchloroformate. Stirred for 20 minutes and 9.6 g. (0.1469 M.) $NaN_3$ (CAUTION!) in 250 ml. water was added slowly with stirring for 2 hours at 0°–5° C. (two layers). The solution was diluted with 500 ml. water and the THF evaporated at 30° C. (15 mm.). The mixture was then extracted three times with 500 ml. ether. Benzene (500 ml.) was added and the solution was dried over anhydrous $MgSO_4$. After filtering away the $MgSO_4$, 30.4 ml. (0.2938 M.) benzyl alcohol was added and the ether was removed by fractional distillation. The residual benzene solution was then heated at reflux for two hours (75°–80° C.) and the benzene was then removed at 45° C. (15 mm.) to leave an oil which was dissolved in 500 ml. CCl₄ and stored at 4° C. for three days to give 9.4 g. (15% yield) solid 1-benzyloxycarbonylaminoethyl-5-diphenylmethylthiotetrazole which was collected by filtration.

K.
1-Benzyloxycarbonylaminoethyl-5-mercaptotetrazole

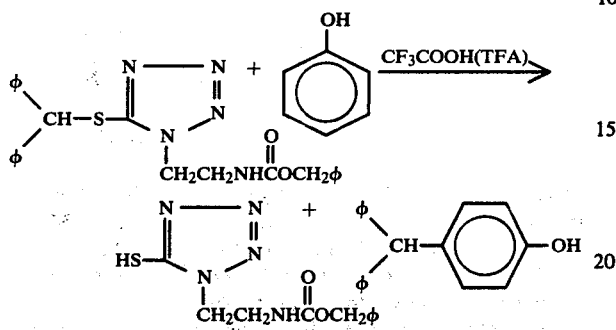

TEA (63 ml.) was added to 9.4 g. (0.0211 M.) of 1-benzyloxycarbonylaminoethyl-5-diphenylmethylthiotetrazole and 9.4 g. (0.1 M.) phenol and left standing at room temperature for 3½ hours. The TFA was then evaporated off at 40° C. (15 mm.). The resulting oily residue was added to 63 ml. of a 5% NaHCO₃ solution and 30 ml. of ether and titrated with concentrated NaOH to pH 8.2. The phases were separated and the aqueous water phase was titrated to pH 2 with concentrated hydrochloric acid, extracted twice with 60 ml. ether and the ether was evaporated to give an oil. The oil was azeotroped with ethyl acetate and crystallized by scratching with a glass rod to give 1-benzyloxycarbonylaminoethyl-5-mercaptotetrazole which was washed with 100 ml. "Skellysolve-B". 3.67 g. (62% yield) was collected by filtration.

L.
1-Aminoethyl-5-mercaptotetrazole.HBr

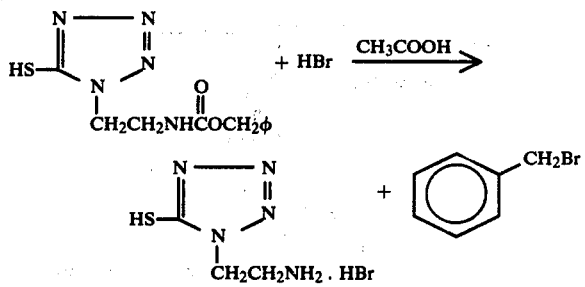

18.25 ml. 30% HBr in glacial acetic acid solution was added to 3.65 g. (0.013 M.) 1-benzyloxycarbonylaminoethyl-5-mercaptotetrazole. There was immediate evolution of CO₂ and a complete solution formed followed by a precipitate upon stirring for one hour. The precipitate was collected by filtration, washed with 30% HBr-HAc solution and then with ether (250 ml.) to give a first crop of 1-aminoethyl-5-mercaptotetrazole.HBr (2.08 g.; 72% yield) containing about 12% benzyl bromide by NMR.

The filtrate and washes from above were left standing at room temperature for 18 hours to give a second crop of 1-aminoethyl-5-mercaptotetrazole.HBr which was collected by filtration and washed with ether. Yield: 0.8 g. (27%) containing about 4% benzyl bromide by NMR. Total yield of pure compound was 89%.

M.
1-(2'-t-Butoxycarbonylaminoethyl)-5-mercaptotetrazole

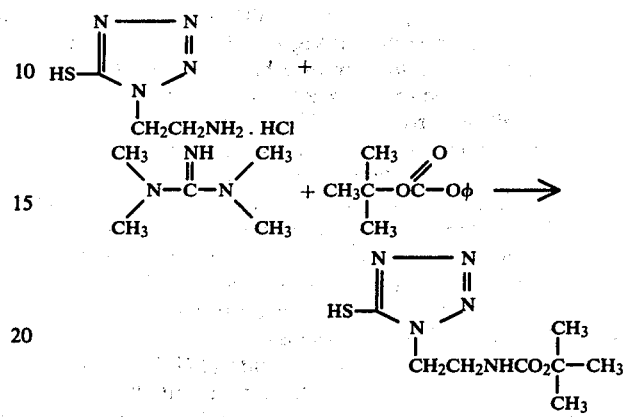

1-Aminoethyl-5-mercaptotetrazole.HCl, 45.6 g. (0.2510 M.) was dissolved in 200 ml. dimethylsulfoxide (DMSO) 64 ml. (57.8 g.; 0.502 M.) 1,1,3,3-tetramethylguanidine and 51.4 ml. (53.6 g.; 0.2761 M.) t-butylphenylcarbonate were added and the solution was stirred at room temperature for 42 hours.

After stirring the solution was diluted with 1500 ml. water and then extracted with 900 ml. ethyl acetate and the ethyl acetate was discarded. The aqueous layer was then stirred with 900 ml. fresh ethyl acetate and acidified to pH 2 with concentrated hydrochloric acid. The layers were separated and the aqueous phase was extracted again with 900 ml. ethyl acetate. The two ethyl acetate extracts were combined and evaporated at 60° C. (15 mm.) for 1 hour to give 47.9 g. of an oil.

The product was crystallized by slurrying with 200 ml. water collected by filtration, washed with 400 ml. water and dried at 30° C. (15 mm.) for 18 hours to give 36.1 g. (59% yield) of 1-(2'-t-butoxycarbonylaminoethyl)-5-mercaptotetrazole.

N.
7-Amino-3-(1-[2'-t-butoxycarbonylaminoethyl]tetrazol-5-ylthiomethyl)-3-cephem-4-carboxylic Acid

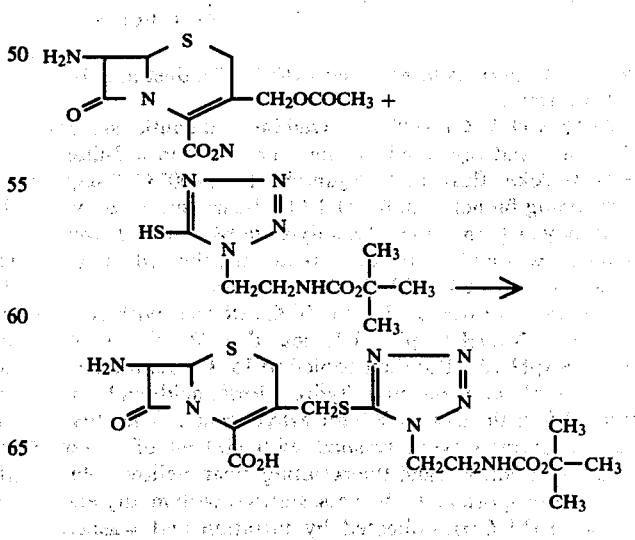

To 900 ml. pH 7 phosphate buffer heated to 45° C. with $N_2$ bubbling through, the following were added in three minutes at 45° C.: 39.1 g. (0.1438 M.) 7-aminocephalosporanic acid; 5.5 g. $NaHSO_3$; 38.8 g. (0.1582 M.) 1-(2'-t-butoxycarbonylaminoethyl)-5-mercaptotetrazole. The nitrogen was then shut off and the mixture was heated to 56° C., titrated to pH 6.6 with $NaHCO_3$ (about 35 g.); and kept at 56° C. for 4 hours (pH 6.3–6.6). After 4 hours at 56° C. the mixture was cooled to 5° C., titrated to pH 5.0 and the resultant solid product was collected by filtration and washed with 100 ml. water to give 35.8 g. (54% yield): [$KF(H_2O)$—32.52% found; 53 g. discounted for 32.5% water] of 7-amino-3-(1-[2'-t-butoxycarbonylaminoethyl]tetrazol-5-ylthiomethyl)-3-cephem-4-carboxylic acid.

DESCRIPTION OF THE PREFERRED EMBODIMENTS

EXAMPLE 1

A.

7-(α-Methoxyiminofurylacetamido)-3-(1-[2'-t-butoxycarboxyaminoethyl]tetrazol-5-ylthiomethyl)-3-cephem-4-carboxylic Acid Sodium α-methoxyiminofuryl acetate (0.63 g.; 3.3 mM.) was suspended in 25 ml. benzene and treated with 4 drops of dry dimethylformamide (DMF). A total of 0.31 ml. (0.46 g., 1.1 eq.) of oxalyl chloride was added and the solution was stirred for 40 minutes at 20° C.

The benzene was removed at 35° C. (15 mm.) and the acid chloride (the gummy residue) was dissolved in 10 ml. acetone (NaCl insoluble). A solution of 1.2 g. (2.6 mM.) 7-amino-3-(1-[2'-t-butoxycarboxyaminoethyl]tetrazol-5-ylthiomethyl)-3-cephem-4-carboxylic acid and 0.7 g. $NaHCO_3$ (pH 7.0) and 2.5 ml. acetone in 20 ml. water was cooled to 3° C. The acetone solution of the above acid chloride was added and the reaction was stirred for 40 minutes at 20° C. (pH 7.0).

The acetone was removed at 40° C. (15 mm.) and the aqueous solution was titrated to pH 1.8 with hydrochloric acid (4 N). The product was extracted three times with 60 ml. ethyl acetate, backwashed with 50 ml. water and azeotroped to dryness at 30° C. (15 mm.). The residue was triturated with 50 ml. ether, collected by filtration and dried in vacuo 18 hours to give 0.88 g. (55% yield) of 7-(α-methoxyiminofurylacetamido)-3-(1-[2'-t-butoxycarboxyaminoethyl]tetrazol-5-ylthiomethyl)-3-cephem-4-carboxylic acid.

Analysis Calculated for $C_{23}H_{28}N_8O_8S_2 \cdot H_2O$ (0.16 M. ether): $KF(H_2O)$, 2.82; C, 44.46; H, 4.99; N, 17.55; S, 10.04. Found: $KF(H_2O)$, 2.41; C, 45.11; H, 4.93; N, 17.00; S, 9.64.

B.

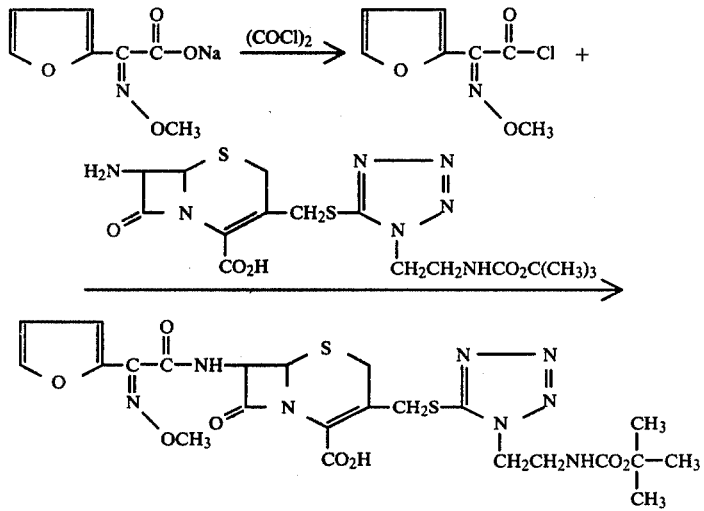

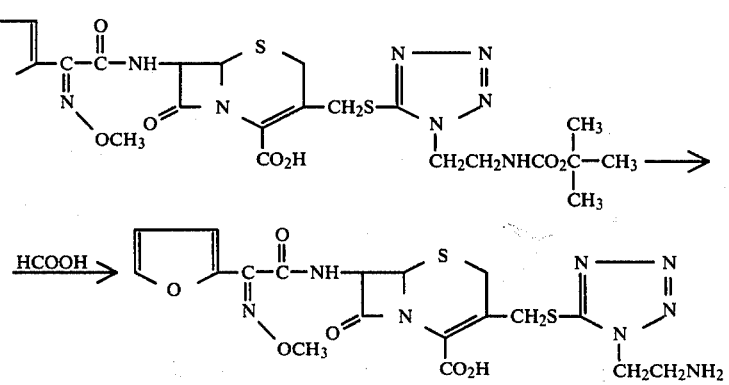

7-(α-Methoxyiminofurylacetamido)-3-(1-[2'-aminoethyl]-tetrazol-5-ylthiomethyl)-3-cephem-4-carboxylic Acid A solution of 400 mg. (0.6571 mM.) 7-(α-methoxyiminofurylacetamido)-3-(1-[2'-t-butoxycarboxyaminoethyl]-tetrazol-5-ylthiomethyl)-3-cephem-4-carboxylic acid in 10 ml. 97% HCOOH (40 mg./ml.) was stirred for 2 hours at room temperature. The excess HCOOH was then evaporated at 30° C. (15 mm.). The residue was azeotroped to dryness three times with 4 ml. ethyl acetate. The residue was triturated with ether, collected by filtration and washed with ether to give 0.36 g. (contaminated with ether, ethyl acetate) of 7-(α-methoxyiminofurylacetamido)-3-(1-[2'-aminoethyl]tetrazol-5-ylthiomethyl)-3-cephem-4-carboxylic acid.

IR and NMR consistent for structure: about 0.4 mole formic acid, about 0.5 mole ethyl acetate and about 0.3 mole ether per mole of product.

3 minutes at 45° C.: 11.16 g. (0.041 M.) 7-ACA, 1.7 g. NaHSO$_3$ and 12.08 g. (0.0492 M.) 1-t-butoxycarbonylaminoethyl-5-mercaptotetrazole. The nitrogen was then shut off and the mixture was heated to 56° C., titrated to pH 6.6 with NaHCO$_3$ (about 8 g.), kept at 56° C. for 4 hours (pH 6.5–6.9), cooled to 5° C., titrated to pH 5.0 and filtered to collect 10.09 g. (54% yield) of 7-amino-3-(1-[2'-t-butoxycarbonylaminoethyl]tetrazol-5-ylthiomethyl)-3-cephem-4-carboxylic acid containing about 10% of 7-ACA by NMR.

B.
7-(α-Methoxyiminofuryl-2-acetamido)-3-(1-[2'-t-butoxycarbonylaminoethyl]tetrazol-5-ylthiomethyl)-3-cephem-4-carboxylic Acid

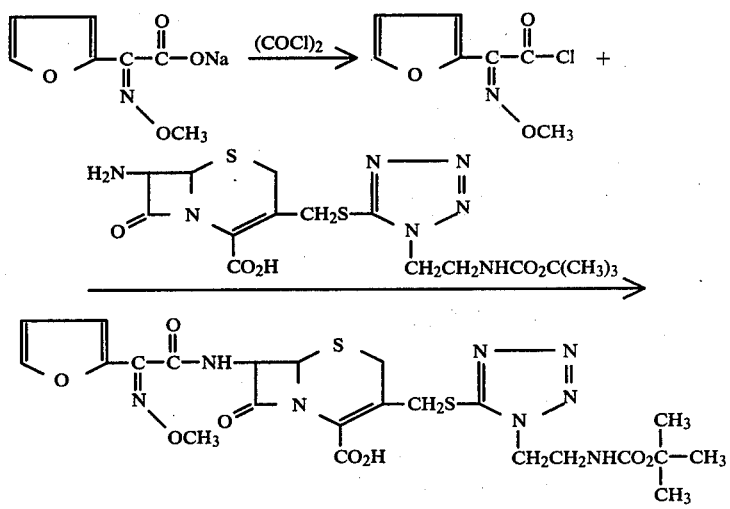

Analysis calculated for C$_{18}$H$_{20}$N$_8$O$_6$S$_2$.H$_2$O [0.5 M HCOOH; 0.5 M ethyl acetate; 0.3 M ether]: KF(H$_2$O), 2.92; C, 42.32; H, 4.90; N, 18.19; S, 10.41. Found: KF(H$_2$O), 3.36; C, 42.47; H, 4.63; N, 18.39; S, 10.07.

EXAMPLE 2

A.
7-Amino-3-(1-[2'-t-butoxycarbonylaminoethyl]tetrazol-5-ylthiomethyl)-3-cephem-4-carboxylic Acid

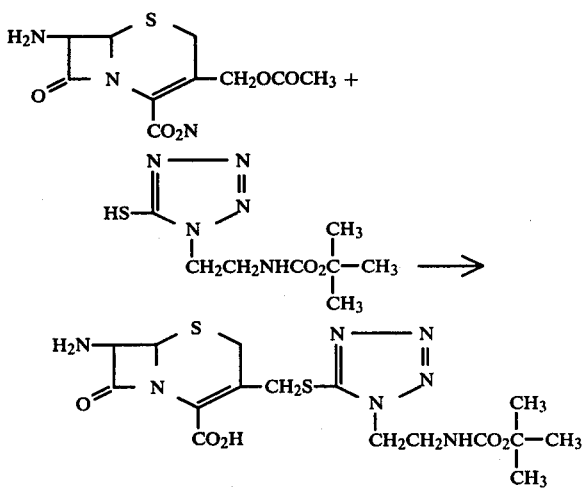

To 258 ml. pH 7 phosphate buffer heated to 45° C. with N$_2$ bubbling through, the following were added in Sodium α-methoxyiminofurylacetate (1.26 g.; 6.6 mM.) was suspended in 50 ml. of benzene and treated with 8 drops of dry DMF. A total of 0.62 ml. (1.1 eq.) of oxalyl chloride was added and the solution was stirred for 40 minutes at 20° C.

The benzene was removed at 35° C. (15 mm.) and the acid chloride (the gummy residue) was dissolved in 20 ml. acetone (NaCl insoluble). A solution of 2.4 g. (5.25 mM). 7-amino-3-(1-[2'-t-butoxycarbonylaminoethyl]-tetrazol-5-ylthiomethyl)-3-cephem-4-carboxylic acid and 1.6 g. NaHCO$_3$ (pH 7.0) and 5 ml. of acetone in 40 ml. of water was cooled to 3° C. The acetone solution of the above acid chloride was added and the reaction was stirred for 40 minutes at 20° C. (pH 7.0).

The solution was titrated to pH 1.8 with hydrochloric acid, extracted three times with 120 ml. ethyl acetate, backwashed with 100 ml. water and azeotroped to dryness at 30° C. (15 mm.). The residue was triturated with 100 ml. ether, collected by filtration and dried under vacuum to give 2.38 g. (74% yield) of 7-(α-methoxyiminofuryl-2-acetamido)-3-(1-[2'-t-butoxycarboxyaminoethyl]tetrazol-5-ylthiomethyl)-3-cephem-4-carboxylic acid.

C.
7-(α-Methoxyiminofurylacetamido)-3-(1-[2'-aminoethyl]-tetrazol-5-ylthiomethyl)-3-cephem-4-carboxylic Acid

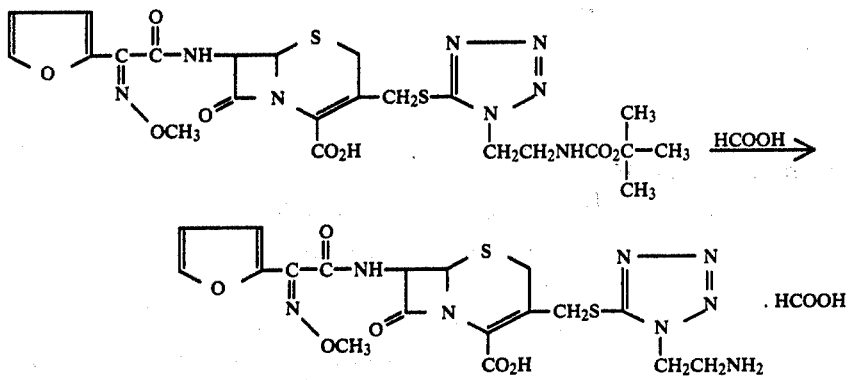

A solution of 2.64 g. (4.34 mM.) of 7-(α-methoxyiminofuryl-2-acetamido)-3-(1-[2'-t-butoxycarboxyaminoethyl]-tetrazol-5-ylthiomethyl)-3-cephem-4-carboxylic acid in 66 ml. 97% HCOOH (40 mg./ml.) was stirred for 2 hours at 20° C. The excess HCOOH was then evaported at 30° C. (15 mm.). The residue was azeotroped to dryness three times with 20 ml. ethyl acetate. The residue was triturated with ether, collected by filtration and washed with ether to give 2.24 g. of 7-(α-methoxyiminofurylacetamido)-3-(1-[2'-aminoethyl]tetrazol-5-ylthiomethyl)-3-cephem-4-carboxylic acid (contaminated with ether and ethyl acetate and formic acid).

Analysis calculated for $C_{18}H_{20}N_8O_6S_2.H_2O$ [0.5 M. HCOOH; 0.5 M. ethyl acetate; 0.3 M. ether]: $KF(H_2O)$, 2.92; C, 42.32; H, 4.90; N, 18.19; S, 10.41. Found: $KF(H_2O)$, 1.67; C, 43.20; H, 4.38; N, 17.90; S, 10.64.

EXAMPLE 3

Substitution of an equimolar weight of sodium-2-ethoxyimino-2-(fur-2-yl)acetate for the sodium-2-methoxyiminofuryl acetate used in the procedure of Example 1 produces 7-(2-ethoxyimino-2-furylacetamido)-3-(1-[2'-aminoethyl]tetrazol-5-ylthiomethyl)-3-cephem-4-carboxylic acid.

EXAMPLE 4

Substitution of an equimolar weight of sodium-2-n-propoxyimino-2-(fur-2-yl)acetate for the sodium-2-methoxyiminofuryl acetate used in the procedure of Example 1 produces 7-(2-n-propoxyimino-2-furylacetamido)-3-(1-[2'-aminoethyl]tetrazol-5-ylthiomethyl)-3-cephem-4-carboxylic acid.

EXAMPLE 5

Substitution of an equimolar weight of sodium-2-n-butoxyimino-2-(fur-2-yl)acetate for the sodium-2-methoxyiminofurylacetate used in the procedure of Example 1 produces 7-(2-n-butoxyimino-2-furylacetamido)-3-(1-[2'-aminoethyl]tetrazol-5-ylthiomethyl)-3-cephem-4-carboxylic acid.

EXAMPLE 6

The products of Examples 1–5 are prepared as syn isomers essentially free of the corresponding anti isomers by the use in the procedures of those examples of purified syn isomers of the appropriate 2-alkoxyimino-2-(fur-2-yl)-acetic acid. Conversion of part of the syn isomer to anti isomer during preparation of the acid chloride from the acid is substantially avoided by minimizing its exposure to hydrogen chloride, e.g. by first converting the acid to its anhydrous sodium salt and by treating that salt with oxalyl chloride under anhydrous conditions in the presence of a hydrogen ion acceptor such as dimethylformamide.

Such syn isomers are also named as (2Z)-2-alkoxyimino-2-(fur-2-yl)acetic acids.

EXAMPLE 7

An injectable pharmaceutical composition is formed by adding sterile water or sterile saline solution (2 ml.) to 100–500 mgm. of 7-[(2Z)-2-methoxyimino-(fur-2-yl)acetamido]-3-(1-[2'-aminoethyl]tetrazol-5-ylthiomethyl)-3-cephem-4-carboxylic acid sodium salt or formate or hydrochloride salt.

Pharmaceutical compositions of the sodium, potassium, formate and hydrochloride salts of the other compounds of the present invention, preferably in the form of the pure syn isomer, are formulated in a similar manner.

When the compounds are first prepared in the form of the free acid they are converted to the desired, highly water soluble potassium salt by treatment with potassium 2-ethylhexanoate in an anhydrous solvent such as n-butanol.

It is occasionally advantageous to have mixed with said solid cephalosporin as a stabilizing and/or solubilizing agent a sterile, anhydrous solid such as sodium carbonate, potassium carbonate or lithium carbonate (e.g. in about 5 or 6 percent by weight of the weight of the cephalosporin) or such as L-lysine, arginine or histidine (e.g. in about 20–50% by weight of the weight of the cephalosporin) or such as a sodium, potassium or calcium salt or levulinic acid, citric acid, ascorbic acid, tartaric acid or pyruvic acid (e.g. in about 25–200% by weight of the weight of the cephalosporin) or such as sodium bicarbonate, ammonium carbamate, alkali metal or ammonium phosphates or N-methylglucamine (per U.K. No. 1,380,741).

There is also provided by the present invention a compound having the formula

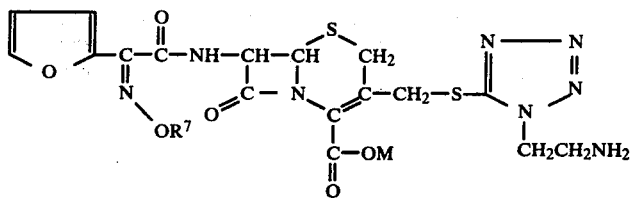

wherein R⁷ is alkyl containing 1–4 carbon atoms and M is

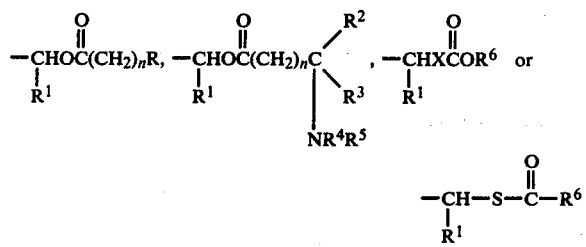

n is 0 to 4; R is hydrogen, alkyl having 1 to 8 carbon atoms, cycloalkyl of 3 to 6 carbon atoms, phenyl, $C_1$–$C_4$ phenalkyl, pyridyl, thienyl, or pyrrolyl; $R^1$ is hydrogen, methyl or ethyl; $R^2$ and $R^3$ are each hydrogen, alkyl having 1 to 6 carbon atoms, phenyl, pyridyl, or thienyl; $R^4$ and $R^5$ are each hydrogen or alkyl of 1 to 4 carbon atoms; $R^6$ is alkyl having 1 to 4 carbon atoms, phenyl, phenalkyl having 1 to 4 carbon atoms, pyridyl, thiadiazolyl, amino or $C_1$–$C_4$ alkylamino; X is NH or oxygen; and each phenyl group is unsubstituted or substituted with one or two substituents selected from the group consisting of alkyl having 1 to 6 carbon atoms, alkoxy having 1 to 4 carbon atoms, hydroxy, amino, $NHR^1$, $N(R^1)_2$, nitro, fluoro, chloro, bromo or carboxy, or a nontoxic, pharmaceutically acceptable salt thereof, said compound being at least 75% by weight in the form of its syn isomer and preferably in the form of its syn isomer essentially free of the corresponding anti isomer.

There is also provided by the present invention a compound having the formula

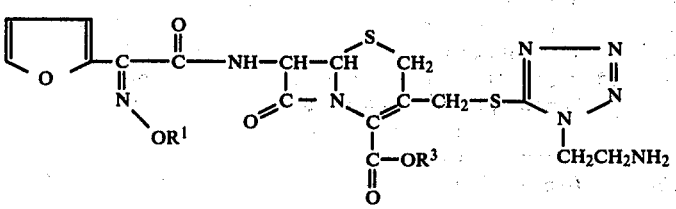

wherein $R^1$ is alkyl containing 1–4 carbon atoms and $R^3$ is selected from the group consisting of

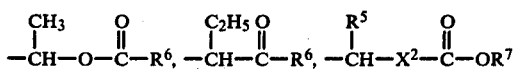

wherein $R^5$ is a hydrogen atom, a methyl or an ethyl group; $X^2$ is —O—, —NH—; $R^6$ is a basic group such as alkyl or aralkyl substituted with substituted or unsubstituted $NH_2$, such as alkyl-$NHCH_3$, aralkyl-$NHCH_3$,

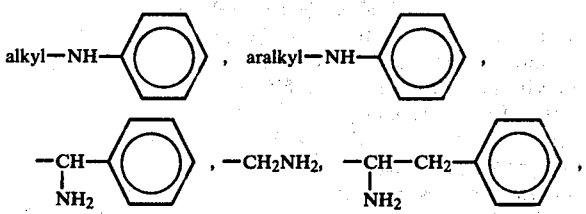

$R^7$ is an alkyl group such as a methyl, ethyl, propyl, isopropyl, butyl, isobutyl, pentyl or 2-ethylhexyl group; a cycloalkyl group such as cyclopropyl, cyclobutyl, cyclopentyl, cyclohexyl or cycloheptyl; an aryl group such as phenyl or naphthyl; an aralkyl group such as benzyl or naphthylmethyl; a heterocyclic group and wherein the alkyl, cycloalkyl, aryl, aralkyl and heterocyclic groups may be substituted with one or more groups selected from the class consisting of amino groups, substituted amino groups such as methylamino, diethylamino or acetamido groups, the halogen groups such as fluorine, chlorine or bromine, nitro groups, alkoxy group such as methoxy, ethoxy, propyloxy, isopropyloxy, butoxy or isobutoxy; or a nontoxic, pharmaceutically acceptable salt thereof, said compound being at least 75% by weight in the form of its syn isomer and preferably in the form of its syn isomer essentially free of the corresponding anti isomer.

There is also provided by the present invention a compound having the formula

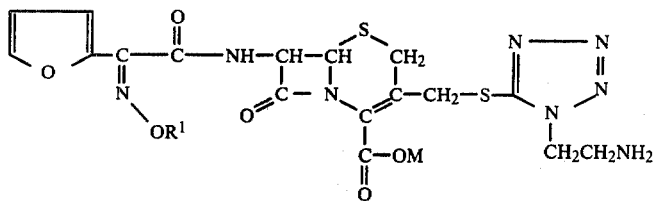

wherein $R^1$ is alkyl containing 1-4 carbon atoms and M is

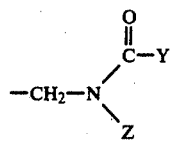

wherein Y is alkyl of one to six carbon atoms, phenyl, benzyl, alkoxy of one to six carbon atoms, or benzyloxy; Z is alkyl of one to six carbon atoms, phenylbenzyl, alkoxy of one to six carbon atoms, cyclopentyl, cyclohexyl and phenyl, or Y+Z taken together are a 3-benzoxazolidine ring; or a nontoxic, pharmaceutically acceptable salt thereof, said compound being at least 75% by weight in the form of its syn isomer and preferably in the form of its syn isomer essentially free of the corresponding anti isomer.

Also included within the present invention are pharmaceutical compositions comprising a mixture of an antibacterially effective amount of a compound of the present invention and a semisynthetic penicillin or another cephalosporin or a cephamycin or a β-lactamase inhibitor or an aminoglycoside antibiotic.

There is further provided by the present invention a pharmaceutical composition comprising an antibacterially effective amount of a compound having the formula

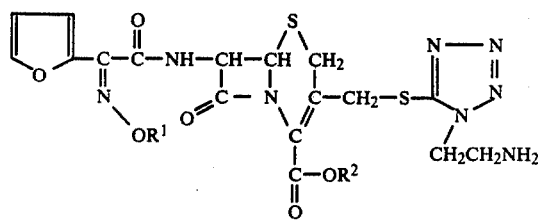

wherein $R^1$ is alkyl containing 1-4 carbon atoms and $R^2$ is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl and preferably is hydrogen or a nontoxic, pharmaceutically acceptable salt thereof, said compound being at least 75% by weight in the form of its syn isomer and preferably in the form of its syn isomer essentially free of the corresponding anti isomer, and a pharmaceutically acceptable carrier therefor.

There is further provided by the present invention a pharmaceutical composition comprising an antibacterially effective amount of the syn isomer of a compound having the formula

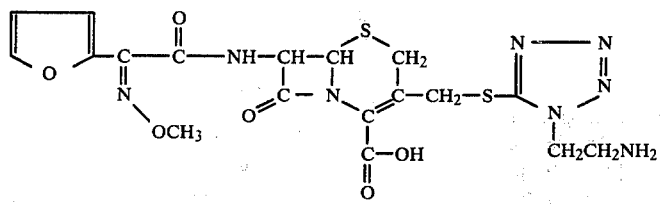

or a nontoxic, pharmaceutically acceptable salt thereof and a pharmaceutically acceptable carrier therefor.

There is further provided by the present invention a method of treating bacterial infections comprising administering by injection to an infected warm-blooded animal, including man, an effective but nontoxic dose of 250-1000 mgm. of a compound having the formula

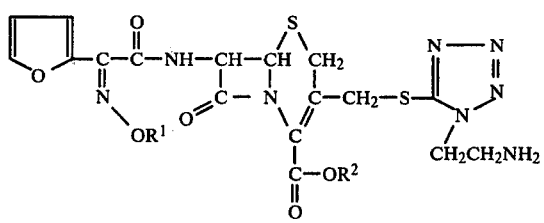

wherein $R^1$ is alkyl containing 1-4 carbon atoms and $R^2$ is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl or a nontoxic, pharmaceutically acceptable salt thereof, said compound being at least 75% by weight in the form of its syn isomer and preferably in the form of its syn isomer essentially free of the corresponding anti isomer.

There is further provided by the present invention a method of treating bacterial infections comprising administering by injection to an infected warm-blooded animal, including man, an effective but nontoxic dose of 250-1000 mgm. of the syn isomer of a compound having the formula

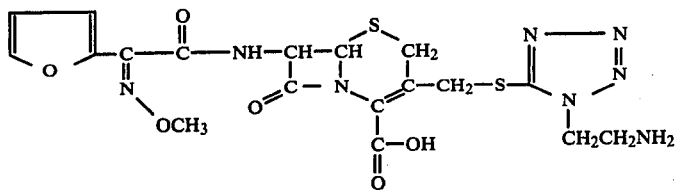

or a nontoxic, pharmaceutically acceptable salt thereof.

There is also provided by the present invention a method for combatting Haemophilus infections which comprises administering to a warm-blooded mammal infected with an Haemophilus infection an amount effective for treating said Haemophilus infection of a composition comprising a compound having the formula

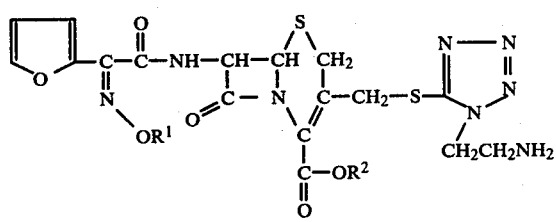

wherein $R^1$ is alkyl containing 1–4 carbon atoms and $R^2$ is hydrogen, pivaloyloxymethyl, acetoxymethyl, methoxymethyl, acetonyl, phenacyl, p-nitrobenzyl, $\beta,\beta,\beta$-trichloroethyl, 3-phthalidyl or 5-indanyl and preferably is hydrogen or a nontoxic, pharmaceutically acceptable salt thereof, said compound being at least 75% by weight in the form of its syn isomer and preferably in the form of its syn isomer essentially free of the corresponding anti isomer, and a pharmaceutically acceptable carrier therefor.

There is also provided by the present invention a method for combatting Neisseria infections which comprises administering to a warm-blooded mammal infected with a Neisseria infection an amount effective for treating said Neisseria infection of a composition comprising a compound having the formula

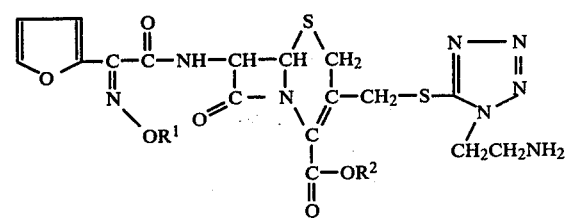

wherein $R^1$ is alkyl containing 1–4 carbon atoms and $R^2$ is hydrogen, pivaloyloxymethyl, acetoxymethyl, methoxymethyl, acetonyl, phenacyl, p-nitrobenzyl, $\beta,\beta,\beta$-trichloroethyl, 3-phthalidyl or 5-indanyl and preferably is hydrogen or a nontoxic, pharmaceutically acceptable salt thereof, said compound being at least 75% by weight in the form of its syn isomer and preferably in the form of its syn isomer essentially free of the corresponding anti isomer, and a pharmaceutically acceptable carrier therefor.

Biological testing was performed according to the procedures described by F. Leitner et al., Antimicrobial Agents and Chemotherapy 10(3), 426–435 (September, 1976).

TABLE 1

| | Antibiotic Activity in Nutrient Broth | | | | |
|---|---|---|---|---|---|
| | | MIC (mcg./ml.) | | | |
| Organism | | Compound of Example 1B | Cefuroxime | Compound of Example 1B | Cefuroxime |
| S. pneumoniae* | $(10^{-3})$** | 0.008 | 0.004 | 0.004 | 0.004 |
| Str. pyogenes* | $(10^{-3})$** | 0.008 | 0.004 | 0.004 | 0.004 |
| S. aureus Smith | $(10^{-4})$ | 0.5 | 0.13 | 0.5 | 0.5 |
| S. aureus + 50% serum | $(10^{-4})$ | 2 | 2 | 1 | 2 |
| S. aureus BX1633 | $(10^{-3})$ | 0.5 | 0.5 | | |
| S. aureus BX1633 | $(10^{-2})$ | 1 | 0.5 | 0.5 | 2 |
| S. aureus Meth-Res | $(10^{-3})$ | 2 | 2 | >125 | >125 |
| Str. faecalis | $(10^{-4})$ | | | 63 | >125 |
| Sal. enteritidis | $(10^{-4})$ | ≦0.25 | 0.5 | | |
| E. coli Juhl | $(10^{-4})$ | 8 | 4 | 2 | 8 |
| E. coli | $(10^{-4})$ | 8 | 4 | | |
| E. coli | $(10^{-4})$ | | | 2 | 8 |
| K. pneumoniae | $(10^{-4})$ | 1 | 2 | | |
| K. pneumoniae | $(10^{-4})$ | 2 | 2 | 16 | 32 |
| K. pneumoniae | $(10^{-4})$ | | | 32 | 125 |
| Pr. mirabilis | $(10^{-4})$ | 0.5 | 0.5 | 0.5 | 0.5 |
| Pr. morganii | $(10^{-4})$ | 2 | 32 | 1 | 63 |
| Pr. vulgaris | $(10^{-4})$ | | | 0.5 | 1 |
| Pr. rettgeri | $(10^{-4})$ | | | 1 | 16 |
| Ser. marcescens | $(10^{-4})$ | 8 | >125 | 8 | >125 |
| Ent. cloacae | $(10^{-4})$ | 32 | >125 | 16 | >125 |
| Ent. cloacae | $(10^{-4})$ | 0.5 | 1 | | |
| Ent. cloacae | $(10^{-4})$ | 8 | >125 | 8 | >125 |
| Ps. aeruginosa | $(10^{-4})$ | 125 | >125 | 63 | 500 |
| Ps. aeruginosa carb. | $(10^{-4})$ | | | 250 | >1000 |

TABLE 1-continued

Antibiotic Activity in Nutrient Broth

| | MIC (mcg./ml.) | | | |
|---|---|---|---|---|
| Organism | Compound of Example 1B | Cefuroxime | Compound of Example 1B | Cefuroxime |
| Ps. aeruginosa | $(10^{-4})$ | | 125 | 500 |
| Ps. aeruginosa | $(10^{-4})$ | | 125 | 500 |
| Ps. aeruginosa | $(10^{-4})$ | | 63 | 250 |
| Ps. aeruginosa | $(10^{-4})$ | | 125 | 1000 |

*45% AAB + 5% serum + 50% broth listed above.
**Dilution of overnight broth culture.
Cefuroxime is sodium 6R,7R-3-carbzmoyloxymethyl-7-(2Z)-2-methoxyimino(fur-2-yl)acetamidoceph-3-em-4-carboxylate.

TABLE 2

Secondary in vitro Screening Results MIC (mcg./ml)

| Organism | Compound of Example 1B | Cefuroxime |
|---|---|---|
| Enterobacter cloacae | 63 | >125 |
| Enterobacter aerogenes | 4 | 4 |
| Enterobacter cloacae | 4 | 8 |
| Enterobacter species | 2 | 2 |
| Escherichia coli | 8 | >125 |
| Escherichia coli | 2 | 4 |
| Escherichia coli | 2 | 2 |
| Escherichia coli | 8 | 32 |
| Escherichia coli | 4 | 16 |
| Escherichia coli | 2 | 4 |
| Escherichia coli | 2 | 4 |
| Escherichia coli | 0.5 | 125 |
| Klebsiella species | 4 | 8 |
| Klebsiella species | 2 | 2 |
| Klebsiella species | 4 | 4 |
| Providencia stuarti | 4 | 2 |
| Proteus mirabilis | 8 | 4 |
| Proteus mirabilis | 4 | 8 |
| Proteus vulgaris | 8 | >125 |
| Proteus vulgaris | 8 | >125 |
| Proteus vulgaris | 2 | 2 |
| Proteus vulgaris | 0.25 | 0.13 |
| Proteus morganii | 63 | >125 |
| Proteus morganii | 4 | 32 |
| Proteus morganii | 4 | 16 |
| Proteus morganii | 4 | 16 |
| Proteus rettgeri | 0.004 | 0.004 |
| Serratia marcescens | >63 | >125 |
| Serratia marcescens | 4 | 16 |
| Staphylococcus aureus | 0.25 | 0.5 |
| Staphylococcus aureus | 0.5 | 0.5 |
| Staphylococcus aureus | 0.5 | 0.5 |
| Staphylococcus aureus | 0.5 | 0.5 |
| Staphylococcus aureus | 1 | 1 |
| Staphylococcus aureus | 0.5 | 0.5 |
| Staphylococcus aureus | 1 | 1 |
| Staphylococcus aureus | 1 | 0.5 |
| Staphylococcus aureus | 0.5 | 0.5 |
| Staphylococcus aureus | 0.5 | 0.5 |
| Escherichia coli | 4 | 4 |
| Escherichia coli | 2 | 4 |
| Proteus mirabilis | 2 | 1 |
| Proteus mirabilis | 4 | 1 |
| Proteus mirabilis | 4 | 1 |
| Proteus morganii | 2 | 2 |
| Proteus mirabilis | 2 | 1 |
| Proteus morganii | .4 | 63 |
| Proteus vulgaris | 0.25 | 0.25 |
| Proteus vulgaris | 2 | 1 |
| Proteus vulgaris | 2 | 1 |
| Proteus vulgaris | 2 | 2 |
| Proteus mirabilis | 2 | 1 |
| Proteus mirabilis | 2 | 2 |
| Enterobacter aerogenes | 16 | 125 |
| Proteus morganii | 4 | 8 |
| Proteus morganii | 4 | 8 |
| Proteus morganii | 4 | 32 |
| Proteus mirabilis | 2 | 0.5 |
| Proteus mirabilis | 2 | 1 |
| Proteus rettgeri | 0.25 | 0.032 |
| Proteus vulgaris | 2 | 1 |
| Providencia stuartii | 4 | 2 |
| Providencia stuartii | 2 | 2 |
| Providencia stuartii | 1 | 0.5 |
| Pseudomonas aeruginosa | >63 | 125 |
| Serratia marcescens | >63 | >125 |
| Serratia marcescens | 16 | 125 |
| Serratia marcescens | 2 | 16 |
| Serratia marcescens | 4 | 32 |
| Serratia marcescens | 16 | 63 |
| Serratia marcescens | 4 | 32 |
| Serratia marcescens | >63 | >125 |
| Serratia marcescens | >63 | >125 |
| Klebsiella pneumoniae | 2 | 2 |
| Klebsiella pneumoniae | 2 | 2 |
| Klebsiella species | 2 | 2 |
| Klebsiella species | 1 | 1 |
| Klebsiella species | 16 | 16 |
| Klebsiella species | 4 | 4 |
| Klebsiella pneumoniae | 4 | 4 |
| Enterobacter cloacae | 4 | 32 |
| Enterobacter cloacae | 32 | 32 |
| Enterobacter aerogenes | 8 | 125 |
| Proteus rettgeri | 4 | 8 |
| Enterobacter aerogenes | 4 | 4 |
| Enterobacter aerogenes | 4 | 8 |
| Pseudomonas aeruginosa | >63 | 125 |
| Proteus rettgeri | 8 | 63 |
| Proteus rettgeri | 1 | 2 |
| Proteus rettgeri | 16 | 63 |
| Proteus rettgeri | 16 | 125 |
| Proteus rettgeri | 4 | 8 |
| Proteus rettgeri | 2 | 1 |
| Proteus rettgeri | 2 | 0.5 |
| Proteus vulgaris | 32 | 125 |
| Proteus morganii | 2 | 16 |

(Cefuroxime is sodium 6R,7R-3-carbamoyloxymethyl-7-(2Z)-2-methoxyimino(fur-2-yl)acetamidoceph-3-em-4-carboxylate.

TABLE 3

Secondary in vitro Screening Results MIC (mcg./ml.)

| Organism | Compound of Example 1B | Ampicillin | Cefuroxime |
|---|---|---|---|
| Hemophilus influenzae | 0.5 | 0.5 | 1 |
| Hemophilus influenzae | 0.5 | 0.5 | 1 |
| Hemophilus influenzae | 0.5 | 0.25 | 0.5 |
| Hemophilus influenzae | 0.25 | 0.25 | 1 |
| Hemophilus influenzae | 0.25 | 0.13 | 0.5 |
| Hemophilus influenzae | 0.5 | 0.25 | 0.5 |
| Hemophilus influenzae | 0.5 | 0.25 | 0.5 |
| Hemophilus influenzae | 0.5 | 0.25 | 0.5 |
| Neisseria gonorrhoeae | 1 | 0.25 | 1 |
| Neisseria gonorrhoeae | 0.063 | 0.13 | 0.016 |
| Neisseria gonorrhoeae | 0.032 | 0.13 | 0.32 |
| Neisseria gonorrhoeae | 0.032 | 0.063 | 0.032 |
| Neisseria gonorrhoeae | 0.13 | 0.13 | 0.063 |

TABLE 3-continued

Secondary in vitro Screening Results MIC (mcg./ml.)

| Organism | Compound of Example 1B | Ampicillin | Cefuroxime |
|---|---|---|---|
| Neisseria gonorrhoeae | 0.13 | 0.13 | 0.13 |
| Neisseria gonorrhoeae | 0.25 | 0.13 | 0.25 |
| Neisseria gonorrhoeae | 1 | 0.25 | 0.25 |
| Neisseria gonorrhoeae | 1 | 0.5 | 1 |
| Neisseria gonorrhoeae | 1 | 0.25 | 0.5 |
| Neisseria gonorrhoeae | 1 | 0.5 | 2 |
| Neisseria gonorrhoeae | 0.13 | 0.25 | 0.13 |
| Neisseria gonorrhoeae | 0.13 | 0.13 | 0.13 |
| Neisseria gonorrhoeae | 0.13 | 0.25 | 0.25 |
| Neisseria gonorrhoeae | 0.25 | 0.063 | 0.13 |
| Haemophilus influenzae | 0.5 | 63 | 0.5 |
| Haemophilus influenzae | 0.25 | 8 | 0.25 |
| Haemophilus influenzae | 0.5 | 63 | 0.5 |
| Haemophilus influenzae | 0.25 | 63 | 0.5 |
| Haemophilus influenzae | 0.5 | 63 | 1 |
| Haemophilus influenzae | 0.25 | 8 | 1 |
| Haemophilus influenzae | 0.25 | 0.13 | 0.25 |

Cefuroxime is sodium 6R,7R-3-carbamoyloxymethyl-7-(2Z)-2-methoxyimino(fur-2-yl)acetamidoceph-3-em-4-carboxylate.

TABLE 4

Mouse Blood Levels*

| Compound | Blood Levels (mcg./ml.) Hours After (Administration) | | | | Sensitivity Limit (mcg/ml.) | Solubility |
|---|---|---|---|---|---|---|
| | 0.25 | 0.5 | 1 | 1.5 | | |
| Compound of Example 1B | 35 (26.6–46) | 17.9 (13.4–23.9) | 5.4 (4.4–6.7) | <2.5 | 2.5 | susp. |
| Cefuroxime | 34.5 (28.2–42.3) | 26.3 (21.4–32.4) | 7.6 (6.2–9.3) | 3.1 (2.2–4.6) | 1.4 | sol. |
| Compound of Example 1B | 33.6 (30–37.6) | 17.4 (14.8–20.4) | 3.9 (3.1–5.1) | <2.6 | 2.6 | sol. |
| Cefuroxime | 25.6 (19.5–35.5) | 20.6 (14.6–28.9) | 6 (4.3–8.4) | 2.1 (1.5–2.8) | 0.9 | sol. |

*Each group consisted of 6 animals and one blood sample was taken from each animal.
Compounds prepared in phosphate buffer and dosed IM at 40 mgm./kg.
Assay Organism: B. subtilis at pH 6.0
Cefuroxime is sodium 6R,7R-3-carbamoyloxymethyl-7-(2Z)-2-methoxyimino(fur-2-yl)acetamidoceph-3-em-4-carboxylate.

We claim:

1. A compound having the formula

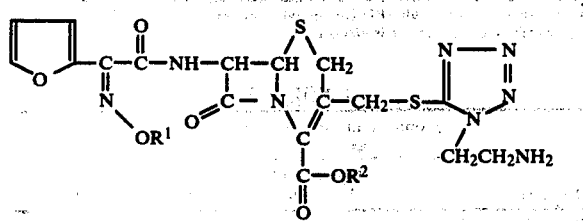

wherein $R^1$ is alkyl of 1–4 carbon atoms and $R^2$ is hydrogen or a conventional, pharmaceutically acceptable, easily hydrolyzed ester forming group; or a nontoxic, pharmaceutically acceptable salt thereof, said compound being at least 75% by weight in the form of its syn isomer.

2. The syn isomer of a compound having the formula

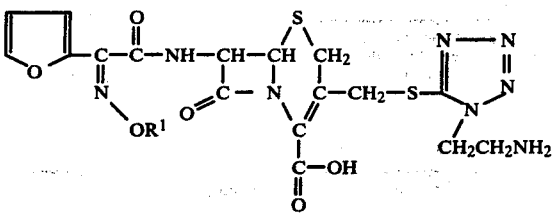

wherein $R^1$ is alkyl of 1 to 4 carbon atoms or a nontoxic, pharmaceutically acceptable salt thereof.

3. The syn isomer of the compound having the formula

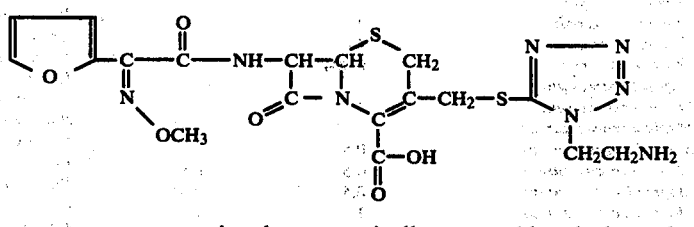

or a nontoxic, pharmaceutically acceptable salt thereof.

4. The syn isomer of the compound having the formula

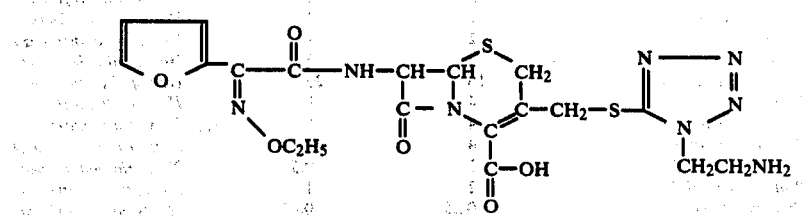

or a nontoxic, pharmaceutically acceptable salt thereof.

5. The syn isomer of a compound having the formula

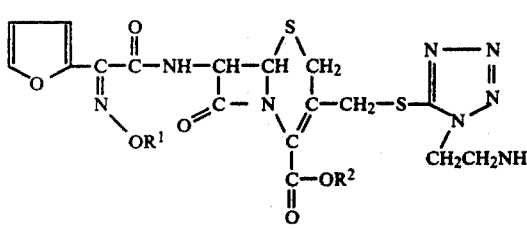

wherein R¹ is alkyl of 1-4 carbon atoms and R² is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl or a nontoxic, pharmaceutically acceptable salt thereof.

6. The syn isomer of a compound having the formula

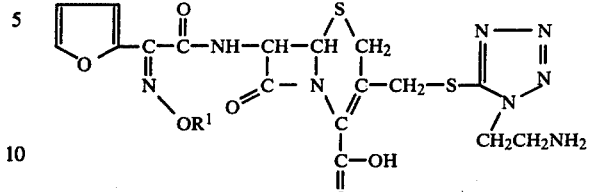

wherein R¹ is alkyl of 1-4 carbon atoms.

7. The syn isomer of the compound having the formula

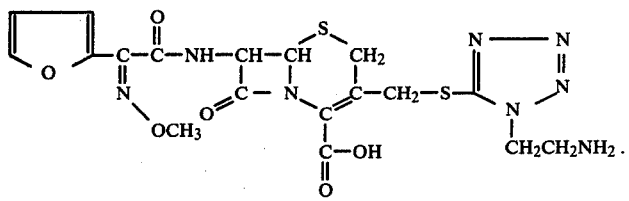

8. The syn isomer of the compound having the formula

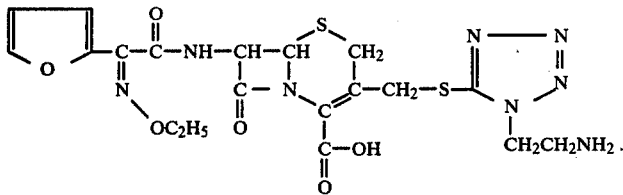

* * * * *